United States Patent [19]

Mendiratta et al.

[11] Patent Number: 4,507,509

[45] Date of Patent: Mar. 26, 1985

[54] PURIFICATION OF BISPHENOL-A

[75] Inventors: Ashok K. Mendiratta, Schenectady; Wayne F. Morgan, Mechanicville, both of N.Y.

[73] Assignee: General Electric Company, Schenectady, N.Y.

[21] Appl. No.: 568,017

[22] Filed: Jan. 4, 1984

[51] Int. Cl.$^3$ .................. C07C 37/68; C07C 39/16
[52] U.S. Cl. .................... 568/724; 568/749
[58] Field of Search .......................... 568/724

[56] References Cited

U.S. PATENT DOCUMENTS 3,277,183 10/1966 Heller et al. ............ 568/724
3,326,986 6/1967 Dugan et al. ........... 568/724
4,408,087 10/1983 Li .......................... 568/724

FOREIGN PATENT DOCUMENTS 142936 9/1982 Japan ...................... 568/724

Primary Examiner—Werren B. Lone
Attorney, Agent, or Firm—Richard J. Traverso; James C. Davis, Jr.; James Magee, Jr.

[57] ABSTRACT

A method for purifying water-crystallized bisphenol-A involving treatment with an aqueous alkaline solution. The concentration of base preferably ranges from 0.1 to 25 weight percent of crude bisphenol-A. The crude bisphenol-A is a solid and preferably at a temperature in the range of about 10° to 80° C.

12 Claims, No Drawings

PURIFICATION OF BISPHENOL-A

CROSS REFERENCE TO RELATION APPLICATION

Reference is made to copending application Ser. No. 443,344 filed Nov. 15, 1982, assigned to the same assignee as the present invention.

BACKGROUND OF THE INVENTION

This invention is concerned with the purification of 2,2-bis(4-hydroxyphenyl) propane (herein identified as "bisphenol-A" or "BPA"). More particularly, this invention is directed to a method of recovering bisphenol-A in a purified state from crude bisphenol-A by treatment with an aqueous alkaline solution.

Crude bisphenol-A is the isolated product of commercial processes for preparing bisphenol-A. It is a mixture of bisphenol-A and impurities derived from a BPA synthesis reaction. An example of a BPA synthesis reaction is the acid-catalyzed condensation of phenol and acetone, where phenol and acetone react in the presence of an acidic material, such as sulfuric acid, hydrochloric acid, cation exchange resin, etc.

The crude bisphenol-A produced contains undesirable impurities such as phenol, 2-(4-hydroxyphenyl)-2-(2-hydroxyphenyl) propane having the formula

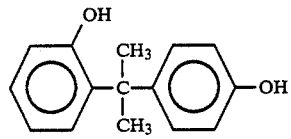

a trishydroxyphenyl compound of the formula

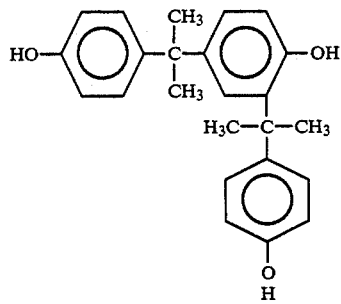

small amounts of other impurities such as the two compounds having formulas

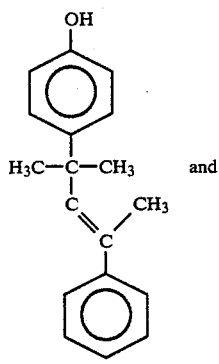 and

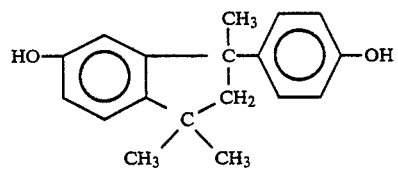

and some impurities which discolor the crude bisphenol-A with unknown structure (herein identified as color bodies).

Since bisphenol-A is used in making polycarbonate resins by reaction of the former with either phosgene or diphenyl carbonate, or for making epoxy resins, both resins being used extensively in commercial applications involving molding, casting and sheet forming processes, it is highly important that the monomeric bisphenol-A used to make such resins be as pure as possible in order to avoid adverse effects on the properties of the polymers thus obtained.

The preparation of bisphenol-A by the acid catalyzed reaction of phenol and acetone is usually carried out in excess phenol (2 or more moles per mole of acetone). This reaction mixture is either subjected to a series of distillation steps to remove substantially all phenol, acetone and water or the acetone and water are removed and the bisphenol-A product is crystallized in the presence of phenol, followed by stripping of the phenol. Both procedures provide crude bisphenol-A which is the starting point for making bisphenol-A of high purity. Distillation or stripping of the phenol from the reaction mixture can be carried out only to a limited extent on account of the thermal instability of the bisphenol-A product.

A conventional method of recovering pure bisphenol-A product from crude bisphenol-A involves crystallization in the presence of an organic solvent. The crude molten bisphenol-A is first dissolved in a suitable organic solvent and the solution is then cooled to yield pure bisphenol-A crystals, which are recovered by filtration. However, this process suffers in that (1) the crystals produced are fine, powdery and needle-like and are difficult to handle, store and dry; (2) these crystals permit some impurities and organic solvent to occlude during crystallization, these impurities cannot be removed during the drying step and hence they are present in the polymerization process and (3) these processes require the use of organic solvent.

A method which uses water as a crystallization medium for crude bisphenol-A is described in U.S. Pat. Nos. 3,326,986 and 3,277,183. According to the disclosure in U.S. Pat. No. 3,326,986, the isolated crude bisphenol-A in molten form is purified by first mixing with water and cooling the mixture to yield large, rhombic crystals of bisphenol-A. The crystallization in water does not provide purification; however, separation of these crystals from the mother liquor, followed by an organic solvent wash, results in purified bisphenol-A. Although the process described within the above-referenced patent avoids occlusion by an organic solvent during the crystal formation step and yields large, less needle-like crystals that are easy to handle, the purification obtained is limited and large quantities of organic solvent are required to wash the crystals.

The disclosure in U.S. Pat. No. 3,277,183 teaches that crystallizing crude bisphenol-A in hot water containing sodium hydroxide provides purification of the bisphenol-A. A process described within the above-referenced patent does not require organic solvent to obtain a high degree of purification. However, the crystals obtained are needle-like and difficult to handle and permit occlusion of impurities. Therefore, the purification obtained by this process is limited. In addition, high temperatures are utilized in the presence of caustic, which is undesirable since bisphenol-A is subject to increased degradation or cracking at high temperatures.

The process described in Ser. No. 443,344, referenced above, describes a washing procedure for purifying aqueous crystallized bisphenol-A with a water/organic solvent wash. Although the process provides large, purified crystals of bisphenol-A which are easy to handle, the process comprising this invention provides crystals of high purity and is much simpler to execute due to the absence of organic solvent.

The process comprising this invention provides a method of obtaining large bisphenol-A crystals of high purity without utilizing an organic solvent and with less degradation of bisphenol-A product than the process described in U.S. Pat. No. 3,277,183.

SUMMARY OF THE INVENTION

A method of purifying water-crystallized crude bisphenol-A is provided comprising washing crude bisphenol-A with an aqueous alkaline solution. The concentration of base is typically within the range of 0.1 to 25 weight percent of crude bisphenol-A and is most preferably in the range of 1 to 10 weight percent of crude bisphenol-A.

OBJECTS OF THE INVENTION

An object of the present invention is to purify crude bisphenol-A without utilizing an organic solvent.

Another object of the present invention is to obtain bisphenol-A crystals of high purity of a rhombic shape and large size.

Another object of the present invention is to provide a process for purifying crude bisphenol-A utilizing an aqueous alkaline solution with no significant degradation of bisphenol-A product.

Another object of the present invention is to provide a process for purifying crude bisphenol-A which comprises a relatively small number of simple steps and procedures.

DETAILED DESCRIPTION OF THE PREFERRED EMBODIMENTS

The objects of the present invention, and other objects, are achieved by treating aqueous crystallized crude bisphenol-A with an aqueous alkaline solution.

The crude bisphenol-A produced from a BPA synthesis reaction is typically in the form of a liquid residue as, for example, in the case of crude bisphenol-A produced from the acid-catalyzed condensation reaction with phenol and acetone after the excess phenol, acetone, and water is removed as described above.

Typically the crude bisphenol-A is molten and crystallization can be effected by simply adding water and slowly cooling the mixture to a temperature in the range of 60° to 70° C. The quantity of water used is not critical, but preferably equal to 1 to 2 parts by weight of the quantity of crude bisphenol-A that is crystallized. The molten crude bisphenol-A and water exist in two phases with the liquid crude bisphenol-A phase resting below the water phase. As the mixture cools with agitation, large crystals form and a slurry of BPA crystals and water is produced. All the water immiscible impurities and color bodies adhere to the crystals during crystallization. Essentially only excess phenol is removed from the crystals in this step. It is these impure crystals with which this process is most useful.

This process is also capable of purifying bisphenol-A obtained by other means, such as bisphenol-A which is crystallized from an organic solvent. Bisphenol-A which is crystallized in such a manner is substantially pure since the organic solvent removes a significant quantity of impurities. In such a situation, it is impractical to utilize this process since the purity of the bisphenol-A crystals will not increase significantly. This route to pure bisphenol-A crystals is undesirable due to the large quantities of organic solvent that are required to crystallize the molten crude bisphenol-A.

After the molten crude bisphenol-A is crystallized in the presence of water, a water soluble base is introduced into the water/BPA crystal slurry. The base ionizes impurities, including phenol, isomeric diphenols and triphenols, color bodies, etc. found in crude bisphenol-A. The ionized impurities become soluble in the aqueous medium and are washed from the surface of the crude bisphenol-A crystals.

Suitable alkaline substances which may be utilized to ionize the impurities and increase their water solubility are, for example, alkali metal hydroxides, alkali earth metal hydroxides, carbonates, bicarbonates, ammonium and tertiary amines of the formula $R'_3N$, where $R'$ is a monovalent radical selected from the group consisting of hydrogen, alkyl radicals of from 1 to 8 carbon atoms and aryl radicals of from 6 to 12 carbon atoms. The preferred alkaline substances include sodium hydroxide, potassium hydroxide, calcium hydroxide, ammonia, triethylamine, trimethylamine, and pyridine.

The quantity of base utilized can range between about 0.1 to 25 weight percent of crude bisphenol-A. The quantity of base which obtains maximum purification is dependent on the temperature of the crude bisphenol-A and aqueous alkaline solution. Lower temperatures demand larger quantities of base to maximize purification than the higher temperatures. However, the maximum degree of purification obtained by this process is independent of temperature. The maximum purification which can be obtained at 70° C. is approximately equal to the maximum purification which can be obtained at 20° C. Therefore, to conserve base and maximize purification, high temperatures may be desired. However, degradation of the bisphenol-A will increase at higher temperatures. The quantity of base utilized is preferably in the range between about 1 and 10 weight percent of crude bisphenol-A at temperatures between 10° C. to 80° C. Smaller quantities of base will usually provide a lower degree of purification, particularly at lower temperatures. Utilizing excessive quantities of base will also reduce the purification obtained, especially when quantities in excess of 10 weight percent of crude bisphenol-A are utilized. Within the preferred range, slight variations in the concentration of base will slightly effect the purification obtained. Increasing or decreasing the concentration of base as little as 0.5 weight percent will effect purification. Where maximum purification is desired for a particular temperature of the crude bisphenol-A and aqueous alkaline solution, the quantity of base utilized should be within the preferred range. However, quantities within the preferred range may be excessive and reduce the degree of purification obtained at certain temperatures. For a temperature of about 60° C., maximum purification is expected from quantities of base within the range of about 3.5 to 4.5 weight percent of crude bisphenol-A. For temperatures of about 70° C., maximum purification is expected from quantities of base within the range of about 3.0 to 4.0 weight percent of crude bisphenol-A. For temperatures of about 50° C., quantities of base in the range of 5.0 to 6.0 weight percent of crude bisphenol-A are expected to provide maximum purification. However, as indicated above, conditions which favor maximum purification with small quantities of base may not be desired if the extent of bisphenol-A degradation is high.

The alkaline substance to be added is preferably in an aqueous solution. Adding the alkaline substance directly, such as ammonia gas, is suitable but requires the use of complex equipment. Organic solvents will interfere with the washing process and they also interfere with the ionization and solubilization of impurities.

It is preferable to maintain a crude bisphenol-A as a solid suspended in water when washing with the aqueous alkaline solution. The crude bisphenol-A crystals are preferably in a temperature within the range of about 10° C. to about 80° C. Purification can be obtained at temperatures above the preferred range; however, significant degradation of the bisphenol-A product could result upon exposure to an oxidative atmosphere in the alkaline solution and the maximum degree of purification which can be obtained is reduced. To avoid significant degradation of the bisphenol-A product, an inert atmosphere, such as a nitrogen atmosphere, is maintained above the slurry of crude bisphenol-A and aqueous alkaline solution. The extent of bisphenol-A degradation within the preferred temperature range is substantially less than at temperatures above 80° C.; however, the use of an inert atmosphere is still desirable when operating within the preferred range.

The quantity of water utilized is preferably within the range of about 1 to 5 parts per part of crude bisphenol-A. Quantities outside of this range can be utilized; however, either the effectiveness of the purification is reduced or the efficiency of the process is reduced. Where the aqueous crystallized bisphenol-A is within the aqueous crystallization medium, a concentrated alkaline solution need only be added to the slurry without significantly increasing the volume of water. Where the aqeuous crystallized bisphenol-A is removed from the aqueous medium, a volume of water within the preferred range must be added to the crystals along with the base.

Once the aqueous crystallized crude bisphenol-A is washed with the aqueous alkaline solution, the purified bisphenol-A crystals are removed by employing conventional solid/liquid separation equipment. The purified crystals are typically removed by a basket centrifuge or by filtration. The crystals obtained will be water-wetted with a very low alkaline content. As such, the crystals need not be washed and completely dried if used to form polycarbonate since water and base are utilized in the polymerization process. However, where it is desirable to remove these trace quantities of base, such as when the BPA will be stored for later use, the purified bisphenol-A crystals are washed with water, preferably in a quantity of about 1 to 5 parts per part of bisphenol-A. Washing the crystals with water can be achieved in the separation equipment, such as a filter or centrifuge, or it can be achieved by reslurrying the crystals. When reslurried, the bisphenol-A crystals can be removed from the slurry by applying the same procedure that is utilized to remove the aqueous alkaline solution. Upon separation, the crystals are dried to remove excess water. The slightly water wetted crystals need not be completely dried if used to form polycarbonate. Water is utilized in the polymerization process and its presence in the bisphenol-A starting material will not effect the finished product. Drying the purified BPA may be aided by the use of conventional equipment.

Bisphenolic compounds other than the 2,2-bis-(4-hydroxyphenyl)propane which can be purified in accordance with the process of this invention are, for example, bis(hydroxy-aryl)-alkenes such as 4,4'-dihdroxydiphenyl-methane; 1,1-bis(4-hydroxyphenyl)ethane, propane, butane, isobutane; 2,2-bis(4-hydroxyphenyl)-butane and bis(4-hydroxyphenyl) ether, sulfide, sulfoxide, and sulfone.

The impurities and small quantities of bisphenol-A which are solubilized by the aqueous alkaline solution may be isolated and returned to the BPA synthesis reaction. After the purified crystals are separated from the aqueous alkaline solution, the solution may be neutralized by a stoichiometric quantity of acid. Suitable acids include hydrogen chloride, hydrogen bromide, hydrogen fluoride, acetic acid, formic acid, etc. The impurities and bisphenol-A precipitate out of the aqueous alkaline solution upon neutralization. The precipitate is removed from the neutralized solution and washed with water. The precipitate, which contains bisphenol-A and impurities may be returned to the acid catalyzed condensation reaction where bisphenol-A is produced. The neutralized solution is comprised of water and the salt corresponding to the base started with and the acid utilized in neutralization. The neutralized solution contains only minute quantities of organic species (impurities, phenol and BPA) and can usually be discarded or recycled.

The process comprising this invention has the advantage that the entire purification process, including aqueous crystallization, can take place in one vessel. The crystallized crude bisphenol-A can be washed in the same vessel in which crystallization takes place. Another advantage to this process is its simplicity. Essentially only one step is required to purify the crystal, i.e., the addition of a base to the water/BPA crystal slurry. The aqueous alkaline solution need only be separated to recover purified bisphenol-A crystals.

The purified bisphenol-A product from this process will be free of any organic washing solvent and will only be water wetted. By avoiding the use of organic solvent, the production of substantially pure polycarbonate will be simple and less hazardous. Another advantage to this process is that the crystals produced are large and rhombic in shape. These crystals are easy to handle in the equipment utilized to produce polycarbonate resin. In addition, these crystals approach 100% purity with no impurities being detected by liquid chromatograph analysis, melting point tests and absorbance values. Such crystals are highly desirable in the production of polycarbonate resin.

EXPERIMENTAL

The following experiments were made to illustrate and compare the processes described in U.S. Pat. Nos. 3,326,986 and 3,277,183 with that of the present invention.

The following experiment demonstrates the process described in U.S. Pat. No. 3,326,986. Samples of aqueous crystallized bisphenol-A were obtained by introducing about 200 grams of crude bisphenol-A (96% pure, initial absorbance value=2.00) to about 400 grams of water in a 1000 milliliter flask and cooling the resulting slurry to about 65° C. The flask was equipped with an agitator, a thermometer, baffles and condenser. The crystals were melted by heating the flask to around 100° C. within an oil bath. A nitrogen blanket was maintained over the flask contents during heating. This was followed by cooling (with agitation) to about 65° C. to effect crystallization of the crude bisphenol-A. The contents of the flask were centrifuged in a basket centrifuge to separate the solid crystals. The separated crystals were washed with 400 grams of toluene and then analyzed to determine the quantity of impurities. High pressure liquid chromatography indicated that the crystals contained 0.2 weight percent impurities. The initial absorbance value was measured to determine the quantity of color bodies by determining the light absorbance of a 10% BPA solution in a 10 centimeter cell. The BPA solution contained 5 grams of the washed bisphenol-A crystals and 50 milliliters methanol. The wavelength of light utilized in the test was 350 nm. The initial absorbance value for the washed crystals was 0.25.

The following procedure illustrates the process described in U.S. Pat. No. 3,277,183. 100 grams of impure bisphenol-A (96% purity; initial absorbance value=2.0) was mixed with 150 grams water in a 1000 milliliter flask equipped with an agitator, overhead condenser, and a thermometer. The flask and its contents were heated to about 100° C. in an oil bath. A nitrogen blanket was maintained over the flask contents during heating. Two liquid phases were observed, the top aqueous phase was clear and colorless and the bottom organic phase was highly colored and clear. While maintaining the temperature at about 100° C., a 50% aqueous solution of NaOH was added slowly to the two phase mixture. No noticeable change in color or volume of the two phases was observed until the addition of about 6.4 grams of 50% aqueous NaOH. Further addition of 0.2 grams 50% NaOH resulted in a one phase, clear, colored solution. This solution was cooled gradually while stirring. Small, needle-like crystals were observed at about 83° C. and after cooling the mixture to 75° C., the crystals were separated from the solution with the help of a basket centrifuge. The crystals were washed with 80 grams water and spun to near dryness. A 65% yield of pure BPA product was obtained. The product had an initial absorbance value of 0.30, measured as described above, with 0.05 weight % impurities being detected by high pressure liquid chromatography.

The following examples are provided in order that those skilled in the art may be better able to understand this invention. They are provided to illustrate the invention and are not intended to limit the scope of the invention to their contents.

EXAMPLE I

To 100 grams of crude bisphenol-A (96% purity; initial absorbance value=2.00) were added 150 grams of water in a 1000 milliliter flask. The flask was equipped with an agitator, thermometer and an overhead condensor. The flask and its contents were heated to about 100° C. under a nitrogen blanket in an oil bath until all the solids were melted. A two phase liquid mixture was obtained; the top aqueous phase being clear and colorless and the bottom organic phase being highly colored and clear. The mixture was cooled slowly with agitation, and large, rhombic crystals were observed at about 95° C. When the mixture was further cooled to about 70° C., about 6.6 grams 50% aqueous NaOH was added to the water/BPA crystal slurry. The mixture was agitated and the crystals were separated with the help of a basket centrifuge. The crystals were washed with 80 grams of water and then spun to near dryness. A 75% yield of pure BPA was obtained. The pure BPA product had an initial absorbance value of 0.10, measured as described above, and no impurities were detected by high pressure liquid chromatography.

EXAMPLES II-XI

The following examples illustrate the extent to which purification is dependent on the quantity of base utilized at various temperatures. For each of examples II-XI the following procedure was followed to obtain each sample.

To 100 grams of crude bisphenol-A (96% purity; initial absorbance value=2.00) were added 150 grams of water in a 1000 milliliter flask. The flask was equipped with an agitator, thermometer and an overhead condensor. The flask and its contents were heated to about 100° C. under a nitrogen atmosphere in an oil bath until all the solids were melted. A two phase liquid mixture was obtained; the top aqueous phase being clear and colorless and the bottom organic phase being highly colored and clear. The mixture was cooled slowly and crystals were observed at about 95° C. The mixture was then further cooled to the temperature indicated in Table I. At this temperature, a 50% aqueous NaOH solution was added in a quantity sufficiently high to provide the weight percentage of crude bisphenol indicated in Table I.

The mixture was agitated and the crystals were separated with the help of a basket centrifuge. These crystals were washed with about 80 grams of water and spun to near dryness. The washed bisphenol-A samples obtained were then analyzed by high pressure liquid chromatography and the initial absorbance values were obtained. No impurities were detected by high pressure liquid chromatography and the initial absorbance values obtained appear in Table I.

TABLE I

| | Degree of Purification Obtained from Various Quantities of Base | | |
|---|---|---|---|
| Example | Temp (°C.) | Quantity of NaOH* | I.A.** |
| II | 45 | 2.9 | 0.63 |
| III | 45 | 4.3 | 0.14 |
| IV | 45 | 5.8 | 0.11 |
| V | 45 | 6.5 | 0.17 |
| VI | 60 | 3.25 | 0.18 |
| VII | 60 | 4.0 | 0.12 |
| VIII | 60 | 5.25 | 0.16 |
| IX | 80 | 1.75 | 0.19 |
| X | 80 | 2.5 | 0.11 |
| XI | 80 | 4.25 | 0.21 |

*The quantity of NaOH is represented as the weight percentage of crude bisphenol-A started with.
**I.A. represents the initial absorbance value obtained for the sample and is an indicator of the quantity of color bodies (impurities) in the sample.

EXAMPLES XII-XIII

Two samples of crude bisphenol-A (100 grams, 96% purity, initial absorbance value=2.00) were added to 200 grams and 300 grams of water, respectively, within a 1000 ml flask equipped as were described in Examples II-XI.

Each sample was heated to about 100° C. under a nitrogen atmosphere until all the solids were melted. These mixtures were cooled slowly and crystals were observed at about 95° C. Each mixture was then cooled to about 45° C. and treated with the same quantity of base as utilized in Example V (13 weight percent of crude bisphenol-A). The mixture was agitated and the crystals were separated and washed with 80 gm of water and spun to near dryness. The dried crystals had initial absorbance values as indicated below in Table II.

TABLE II

| | Degree of Purification Obtained Utilizing Various Quanties of Water | | |
|---|---|---|---|
| Example | Quantity of Water* | Quantity of Base** | I.A. |
| V | 1.5 | 6.5 | 0.17 |
| XII | 2 | 6.5 | 0.18 |
| XIII | 3 | 6.5 | 0.17 |

*The quantity of water is represented as a weight ratio of water to crude bisphenol-A started with.
**The quantity of base is represented as the weight percent of crude bisphenol-A started with.

What is claimed is:

1. A process for purifying solid water-crystallized crude bisphenol-A comprising contacting solid water crystallized crude bisphenol-A with an aqueous alkaline solution and recovering said solid water-crystallized crude bisphenol-A in substantially the same form.

2. A method as in claim 1 wherein the aqueous alkaline solution contains a quantity of base that falls within the range of about 0.1 to 25 weight percent of the water-crystallized crude bisphenol-A.

3. A process as in claim 1 wherein the temperature of the water-crystallized crude bisphenol-A and aqueous alkaline solution is maintained within the range of about 10° to 80° C.

4. A process as in claim 1 wherein the base is selected from the group consisting of alkali-earth-metal hydroxides, alkali-metal carbonates, alkali-metal bicarbonates and alkali-metal hydroxides.

5. A process as in claim 1 wherein a nitrogen atmosphere is maintained over the aqueous crystallized crude bisphenol-A during washing.

6. A process in accordance with claim 1 wherein the crude bisphenol-A is crude 2,2-bis(4-hydroxyphenyl)-propane.

7. A process in accordance with claim 1 wherein the quantity of water within the aqueous alkaline solution is in the range of 1 to 5 parts by weight per part of water-crystallized crude bisphenol-A.

8. A process in accordance with claim 1 comprising the additional step of recovering the water-crystallized crude bisphenol-A from the aqueous alkaline solution after washing.

9. A process in accordance with claim 8 further comprising the step of washing the recovered water-crystallized crude bisphenol-A with from 1 to 5 parts by weight water.

10. A process in accordance with claim 1 wherein the base within the aqueous alkaline solution is selected from the group consisting of sodium hydroxide, potassium hydroxide, ammonia, triethylamine, trimethylamine, pyridine and mixtures thereof.

11. A process in accordance with claim 10 wherein the quantity of base within the aqueous alkaline solution is within the range of 1 to 10 weight percent of the water-crystallized crude bisphenol-A.

12. A process in accordance with claim 8 further comprising the steps of (a) neutralizing the aqueous alkaline solution from which the water-crystallized crude bisphenol-A crystals were recovered; (b) removing the solids which form; and (c) recycling said solids to an acid catalyzed condensation reaction for the production of bisphenol-A.

* * * * *